United States Patent
Hale et al.

(10) Patent No.: US 9,615,772 B2
(45) Date of Patent: Apr. 11, 2017

(54) GLOBAL ENDOSCOPIC VIEWING INDICATOR

(75) Inventors: Eric Lawrence Hale, Altadena, CA (US); Nathan Jon Schara, Pasadena, CA (US); Hans David Hoeg, Arcadia, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 2788 days.

(21) Appl. No.: 11/049,003

(22) Filed: Feb. 1, 2005

(65) Prior Publication Data

US 2005/0187432 A1 Aug. 25, 2005

Related U.S. Application Data

(60) Provisional application No. 60/546,261, filed on Feb. 20, 2004.

(51) Int. Cl.
| | | |
|---|---|---|
| *A61B 1/04* | (2006.01) | |
| *A61B 1/00* | (2006.01) | |
| *A61B 5/06* | (2006.01) | |
| *A61B 34/20* | (2016.01) | |
| *A61B 90/00* | (2016.01) | |
| *A61B 34/10* | (2016.01) | |

(52) U.S. Cl.
CPC ............ *A61B 5/065* (2013.01); *A61B 1/0005* (2013.01); *A61B 1/00009* (2013.01); *A61B 1/00183* (2013.01); *A61B 2034/107* (2016.02); *A61B 2034/2048* (2016.02); *A61B 2090/364* (2016.02); *A61B 2090/368* (2016.02)

(58) Field of Classification Search
USPC .................................. 600/101, 103, 107–118
See application file for complete search history.

(56) References Cited

U.S. PATENT DOCUMENTS

| | | | |
|---|---|---|---|
| 3,572,325 A | 3/1971 | Bazell et al. | |
| 3,856,000 A | 12/1974 | Chikama | |
| 4,697,577 A | 10/1987 | Forkner | |
| 5,638,819 A * | 6/1997 | Manwaring et al. | ......... 600/424 |
| 5,762,603 A | 6/1998 | Thompson | |
| 5,776,050 A * | 7/1998 | Chen et al. | ................... 600/117 |
| 5,800,341 A | 9/1998 | Mckenna et al. | |
| 5,907,664 A * | 5/1999 | Wang et al. | .................. 700/251 |
| 6,201,984 B1 * | 3/2001 | Funda et al. | ................. 600/407 |
| 6,241,657 B1 * | 6/2001 | Chen et al. | ................... 600/117 |
| 6,346,940 B1 * | 2/2002 | Fukunaga | ..................... 345/427 |
| 6,371,909 B1 * | 4/2002 | Hoeg et al. | ................... 600/173 |
| 6,500,115 B2 | 12/2002 | Krattiger et al. | |
| 6,529,765 B1 * | 3/2003 | Franck et al. | ............... 600/427 |
| 6,560,013 B1 | 5/2003 | Ramsbottom | |
| 6,663,559 B2 * | 12/2003 | Hale et al. | .................... 600/118 |
| 6,671,581 B2 * | 12/2003 | Niemeyer et al. | ............ 700/245 |
| 6,695,774 B2 | 2/2004 | Hale et al. | |
| 6,850,817 B1 * | 2/2005 | Green | .......................... 700/245 |
| 2001/0029333 A1 * | 10/2001 | Shahidi | ........................ 600/429 |
| 2003/0018235 A1 * | 1/2003 | Chen et al. | ................... 600/109 |
| 2003/0220541 A1 * | 11/2003 | Salisbury et al. | ............ 600/101 |

* cited by examiner

*Primary Examiner* — Anhtuan T Nguyen
*Assistant Examiner* — Alexander Newton
(74) *Attorney, Agent, or Firm* — Whitmyer IP Group LLC (57) ABSTRACT

A graphical model provides a dynamic representation of the endoscopic view and viewing direction relative to a virtual world. The model can be oriented and adjusted to approximate a real world situation. Angular image navigation coordinates are also provided.

12 Claims, 12 Drawing Sheets

Prior Art

Fig. 1

*Prior Art*

GLOBAL ENDOSCOPIC VIEWING INDICATOR

CROSS-REFERENCE TO RELATED APPLICATIONS

This application claims the benefit of U.S. provisional application Ser. No. 60/546,261 filed on Feb. 20, 2004, entitled "Global endoscopic viewing indicator", the contents of which are incorporated herein by reference.

FIELD OF THE INVENTION

The present invention relates to variable direction of view endoscopes.

BACKGROUND OF THE INVENTION

The purpose of variable direction of view endoscopes is to provide greater viewing mobility. Variable direction of view endoscopes come in two general classes: rigid and flexible. Rigid variable direction of view scopes either change their line of sight mechanically, as disclosed in U.S. Pat. No. 3,856,000 to Chikama, U.S. Pat. No. 6,371,909 to Hoeg, U.S. Pat. No. 6,560,013 to Ramsbottom, U.S. Pat. No. 4,697,577 to Forkner, U.S. Pat. No. 6,500,115 to Krattiger et al., and U.S. Pat. No. 5,762,603 to Thompson, or electronically, as disclosed in U.S. Pat. No. 5,313,306 to Kuban, and U.S. Pat. No. 5,800,341 to McKenna et al. Flexible variable direction of view endoscopes, exemplified by U.S. Pat. No. 3,572,325 to Bazell et al., change their line of sight by deflecting the entire distal section of the instrument.

A problem introduced by such variable direction of view endoscopes is that the endoscopic line of sight can not readily be estimated during use because the tip of the endoscope is hidden. Fixed-angle endoscopes do not suffer from this problem because the viewing direction has a fixed relationship to the endoscope shaft and can be mentally extrapolated by the operator as an extension of the endoscope's longitudinal axis. Even with indicator knobs, dials, or markers (as in U.S. patent application 20020099263 and U.S. Pat. No. 6,500,115 to Krattiger et al.) it can be difficult to estimate viewing direction of variable direction of view scopes because the position of the view vector origin is unknown. Getting an external estimate of where the endoscope is "looking" is important as the clinician tries to integrate preexisting knowledge of the anatomy with the viewing process, and this need must somehow be met.

Hale et al. in U.S. Pat. No. 6,663,559 take a step in this direction by providing a computer graphical depiction of a variable direction endoscope and its viewing direction to assist the user in understanding the changing viewing configuration. This depiction is meant to show the dynamic relationship between the shaft and the endoscopic line of sight as it might be seen from an external viewpoint if the endoscope tip were visible during use. While this method gives the operator a view vector direction locator, it does not provide a clear correlation between the live image, its orientation, and the endoscope configuration.

Accordingly, the primary object of the present invention is to provide a dynamic representation of the endoscopic viewing direction featuring a live image icon and a virtual world. Another object is to provide real time numerical indications of the global position of the view relative to a defined equator and zero-meridian. Still further objects and advantages will become apparent from the ensuing description and drawings.

BRIEF SUMMARY OF THE INVENTION

In accordance with the present invention, a variable direction of view endoscope with at least two mechanical degrees of freedom has two generally parallel onboard motors which can rotate two generally parallel shafts for the purpose of achieving variable viewing.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what we presently believe is the best mode of carrying out the invention.

Prior Art Devices

Figure 1:
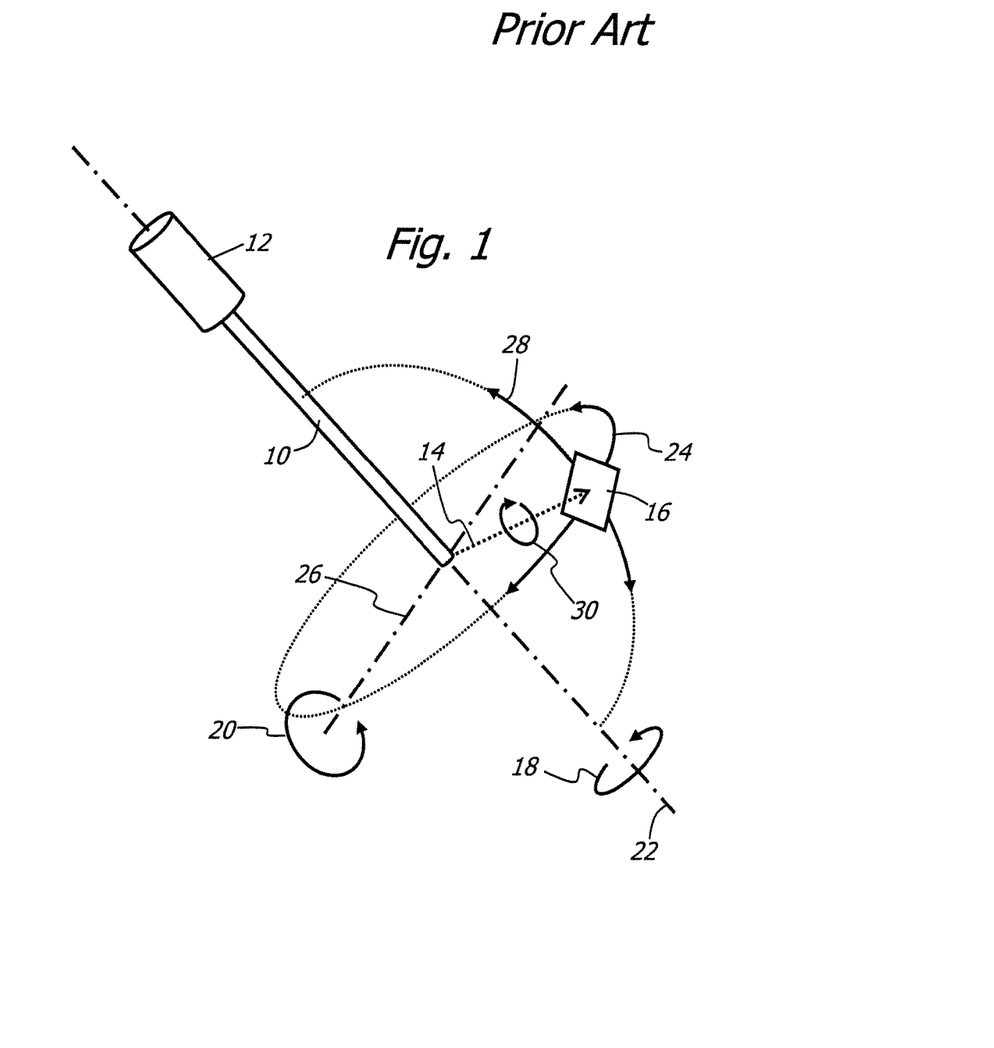
FIG. 1 shows the operating principle of a variable direction of view endoscope.

Referring now to the drawings, in which like reference numbers represent similar or identical structures throughout, FIG. 1 is a diagram of a basic variable direction of view endoscope comprising a shaft 10 and a proximal end 12. Such an endoscope typically has a view vector 14 (and a view field 16) with at least two degrees of freedom 18, 20. The $1^{st}$ degree of freedom 18 permits rotation of the view vector 14 about the endoscope longitudinal axis 22, which allows the view vector 14 to scan in a latitudinal direction 24. The $2^{nd}$ degree of freedom 20 permits rotation of the view vector 14 about an axis 26 perpendicular to the longitudinal axis 22, which allows the view vector 14 to scan in a longitudinal direction 28. A $3^{rd}$ degree of freedom 30 may also be available because it is usually possible to adjust the rotational orientation of the endoscopic image.

Figure 2A:
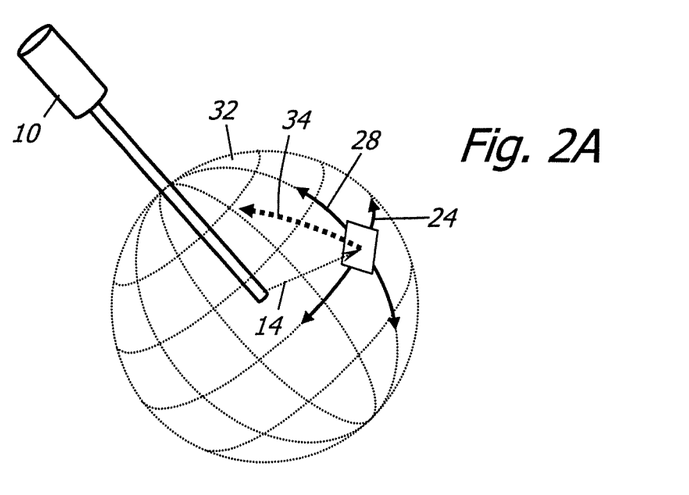
FIGS. 2A and 2B show the concept of endoscope coordinate systems used for viewing navigation.
Figure 2B:
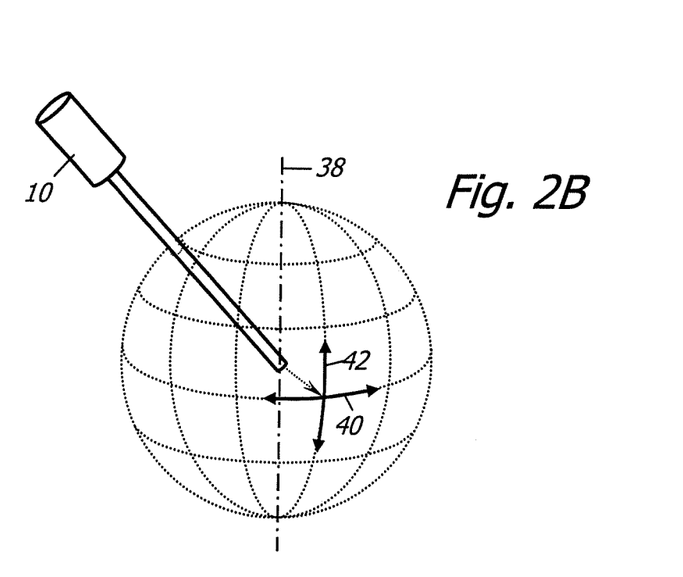

FIG. 2A shows a navigation coordinate system 32 aligned with the principal mechanical axes of the endoscope 10. This is the inherent endoscope frame and is indicative of the of fundamental pan-tilt motion of the view vector 14 according to the $1^{st}$ and $2^{nd}$ degrees of freedom 24, 28. Off-axis moves 34 can be made by a linear combination of these degrees of freedom 24, 28, typically calculated by a computer. Because a computer can calculate such off-axis moves, it can also erect new navigation coordinate systems for the sake of simplifying viewing navigation in certain circumstances. This is illustrated in FIG. 2B, where the navigation coordinate system 32 has been aligned with a local vertical 38. This vertical 38 can be arbitrarily selected, or it can be computed based in outputs from tilt sensors in the endoscope 10. A pure pan 40 or a pure tilt 42 motion in this coordinate system 32 is actually a linear combination of the individual mechanical degrees of freedom 24, 28.

Figure 3:
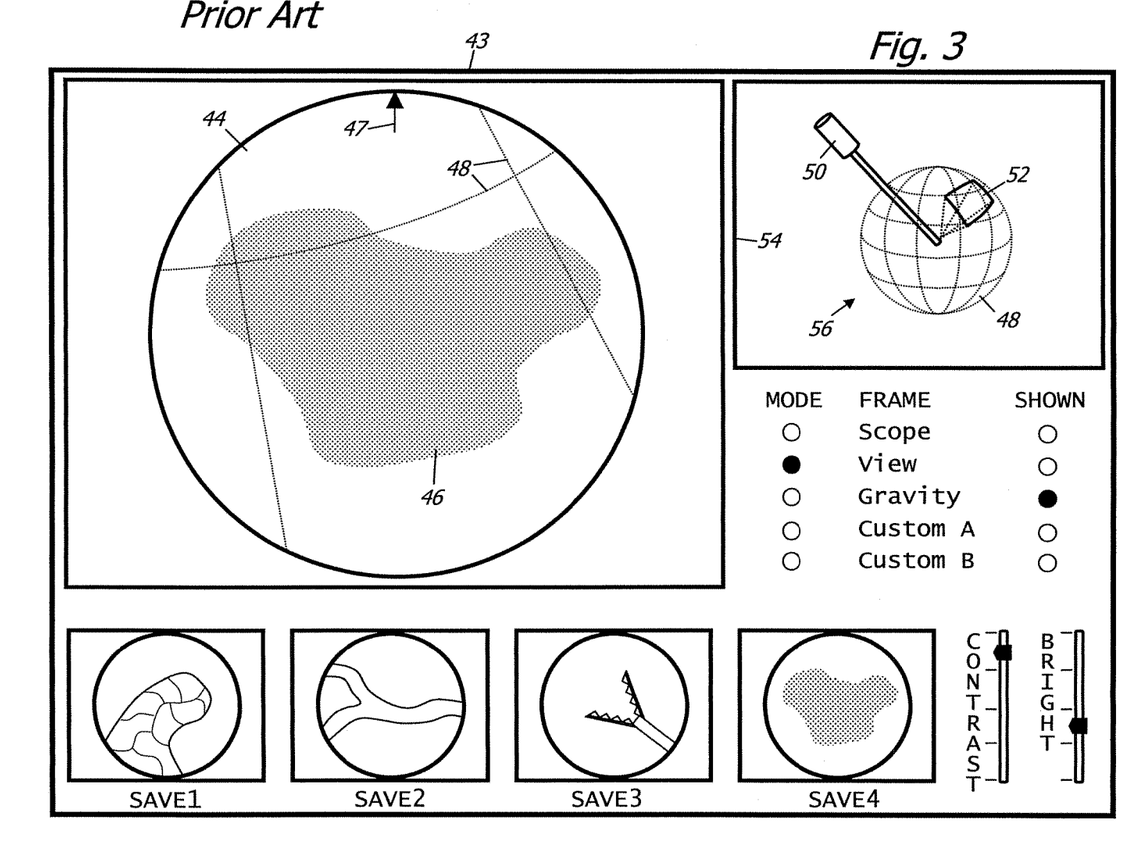
FIG. 3 illustrates a graphical user interface for a variable direction of view endoscope.

The endoscopic image and additional relevant information are presented to the user on a display device. FIG. 3 illustrates an embodiment of this presentation. A section of the screen 43 is used to display the live endoscopic image 44, showing a certain feature 46, with a view-up vector 47. A graphical representation of a navigation coordinate system 48 may be superimposed on the image 44. This coordinate system 48 is also displayed in a separate section of the screen 54 along with graphical representations of the endoscope 50 and its current view cone/pyramid 52. Together these elements constitute a virtual world 56 which shows the endoscopic viewing configuration as seen from a virtual viewpoint outside the world 56. A locally or globally defined view-up vector (not shown) can optionally be displayed on the view cone 52.

Preferred Embodiment

Figure 4A:
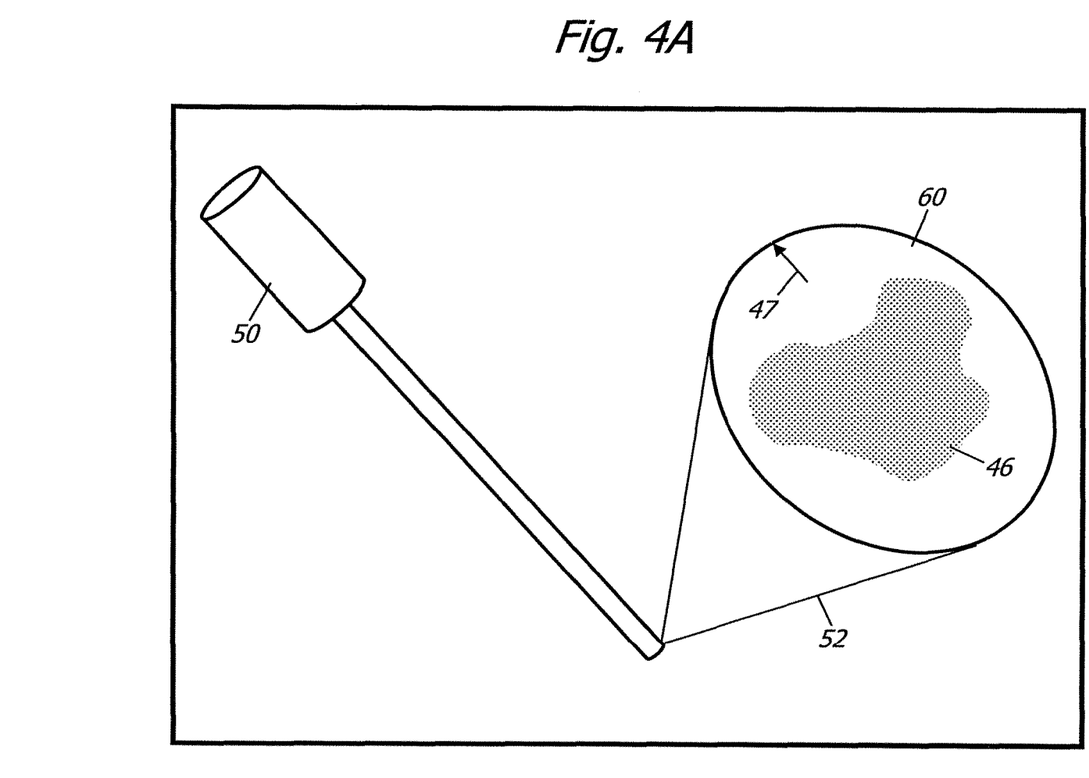
FIG. 4A is a computer graphical depiction of an endoscope, its view cone, and a live video image textured onto the base of the view cone according to the present invention.
Figure 4B:
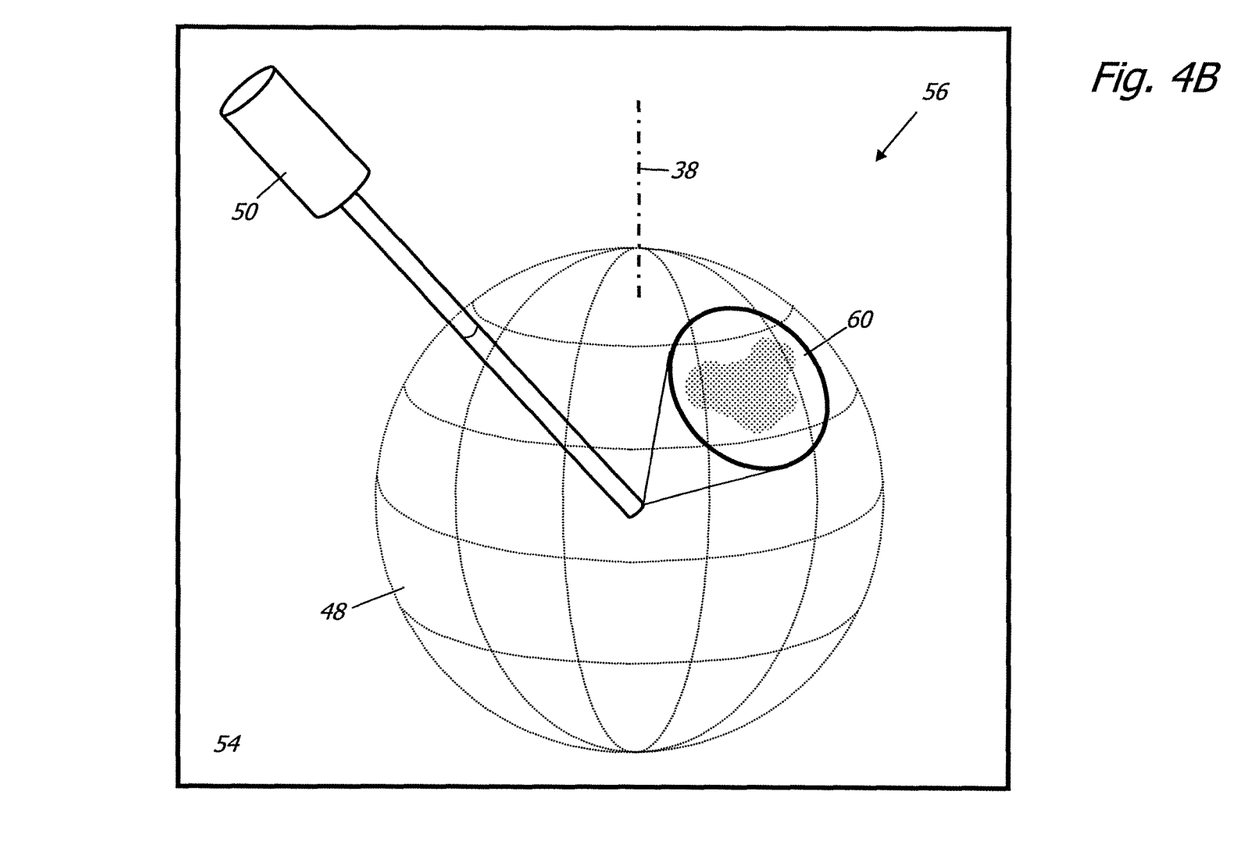
FIG. 4B further includes a global navigation grid.

FIG. 4A shows the virtual endoscope 50 with a texture mapped version of the live endoscopic image 60 at the base of the view cone 52. As the line of sight is changed, the view cone 52 is swept through a solid angle and the textured image 60 is continuously updated while its perspective changes with the changing viewing direction. This dynamic image display gives the operator important information about the physical orientation of the view relative to the viewing direction and the angle of the endoscope. Thus the user can get a feeling for the relative locations and orientations of features seen with the endoscope. Superimposing a navigation coordinate system 48, in FIG. 4B aligned with the direction of gravity 38, further facilitates the operator's ability to correlate the locations and orientations of viewed features with the overall endoscopic space. Note that unless the endoscope has stereoscopic capabilities, the size the virtual world 56 will not be known.

Figure 5A:
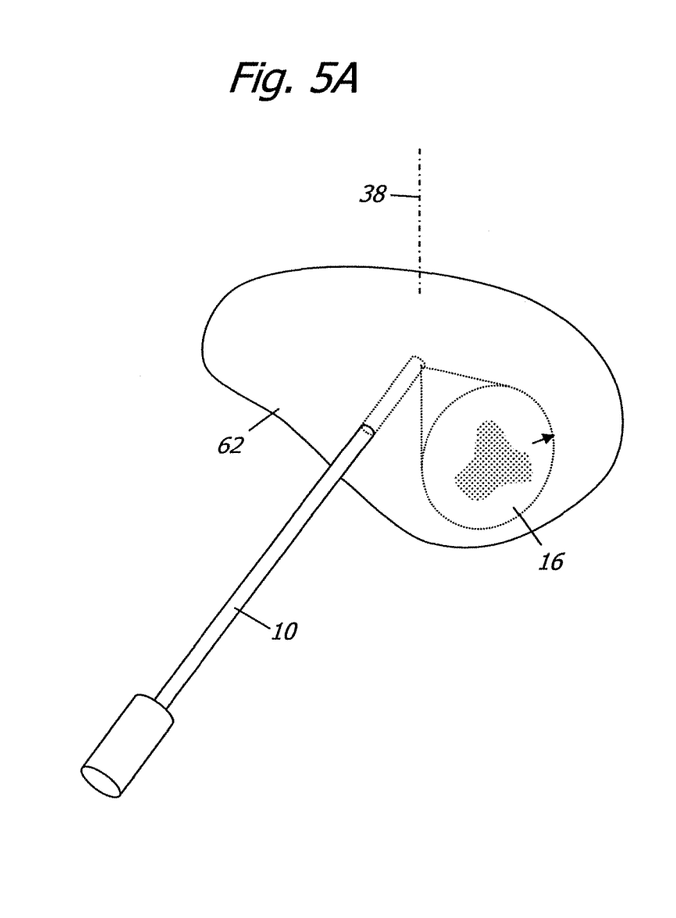
FIGS. 5A and 5B illustrates a graphical depiction of an endoscope and a coordinate system oriented to simulate a real world situation.
Figure 5B:
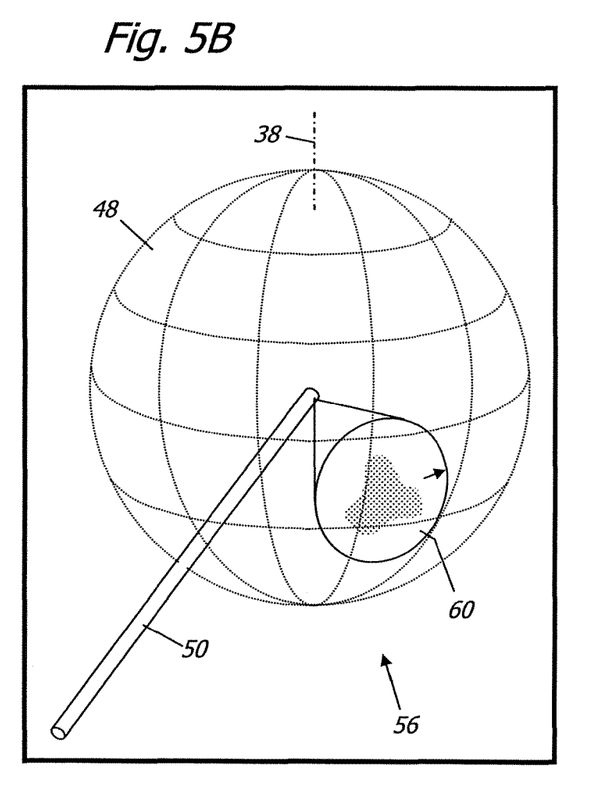

The virtual world 56 can be aligned to represent the actual physical arrangement of the endoscope relative to the endoscopic inspection site, as represented in FIGS. 5A and 5B. FIG. 5A shows the physical arrangement of the endoscope 10, its view 16, and an anatomical part 62 as seen by the operator. FIG. 5B shows a virtual equivalent of this physical arrangement, oriented specifically to approximate the operator's view of the situation. If the endoscope 10 is instrumented with tilt sensors and a gyroscope for sensing the scope's longitudinal location relative to a selected reference, the computer can dynamically align the virtual endoscope 50 and the navigation coordinate system 48 according to the output signals from these sensors. If the endoscope 10 only has tilt sensors, the computer can accurately adjust only the pitch and roll of the virtual endoscope 50. Depending on the viewing navigation mode and coordinate system, the operator can interactively adjust the attitude of the navigation coordinate system 48 with an input device such as a mouse, similar to how a mechanical designer would orient an assembly in a 3D CAD program. Without any sensors, the operator would manually adjust both the virtual scope 50 and navigation coordinate system 48. Regardless of adjustment method, the virtual world 56 can be oriented to represent any real world situation.

Figure 6A:
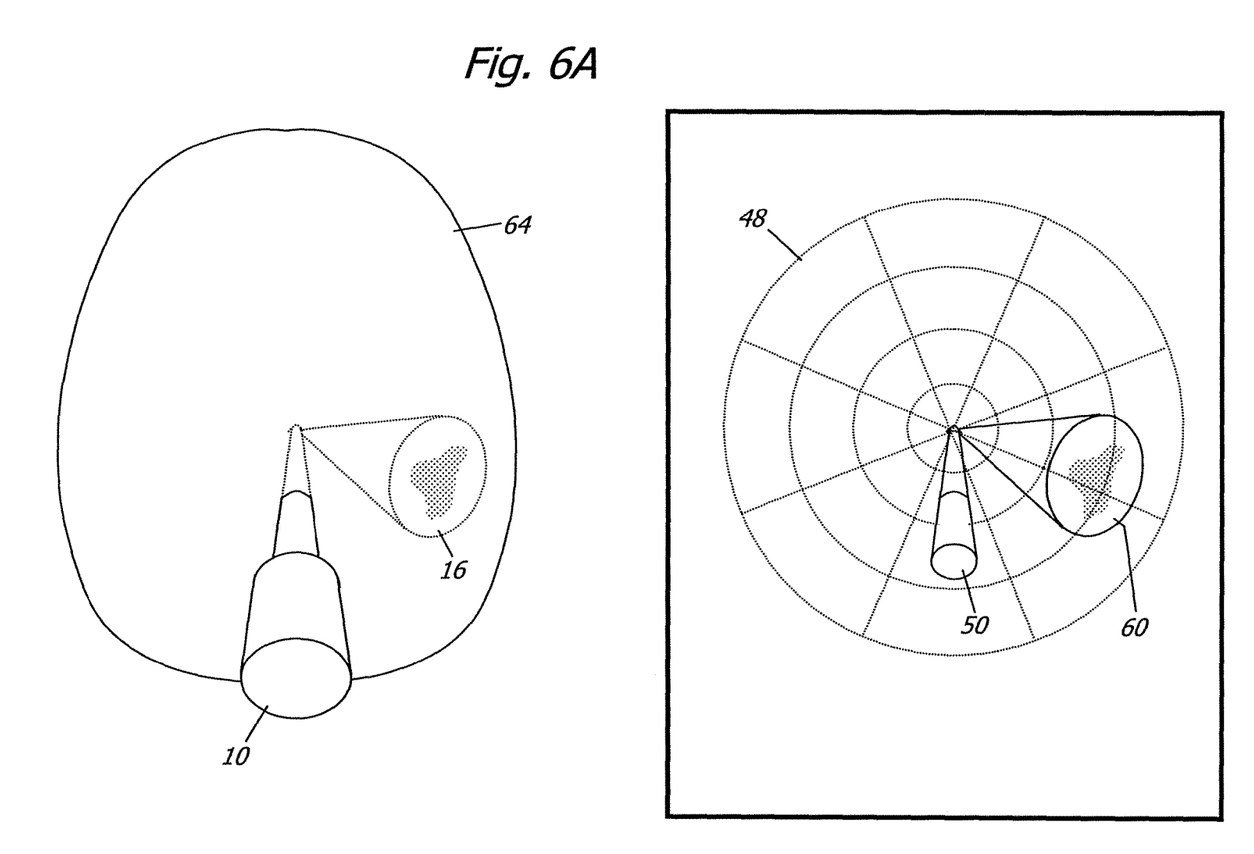
FIGS. 6A, 6B, 6C, 6D, and 6E show graphical depictions oriented to simulated real world surgical situations.
Figure 6B:
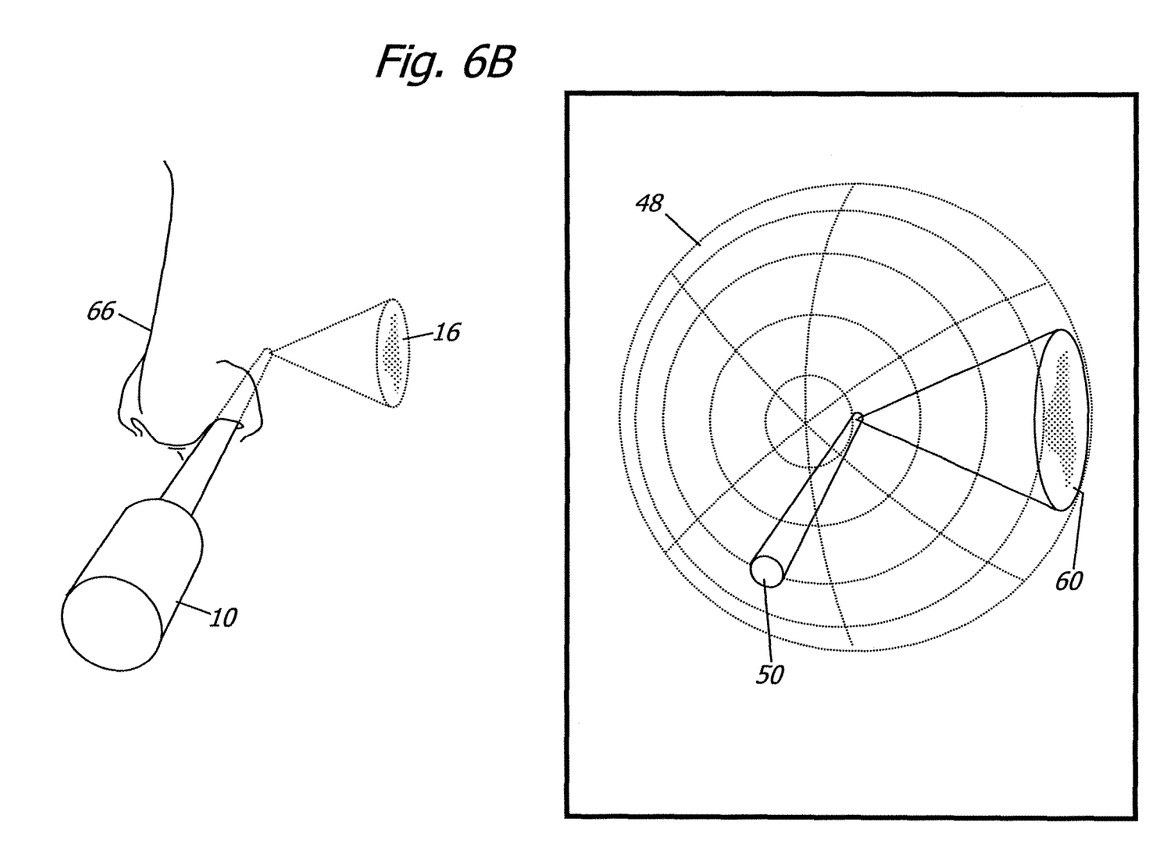
Figure 6C:
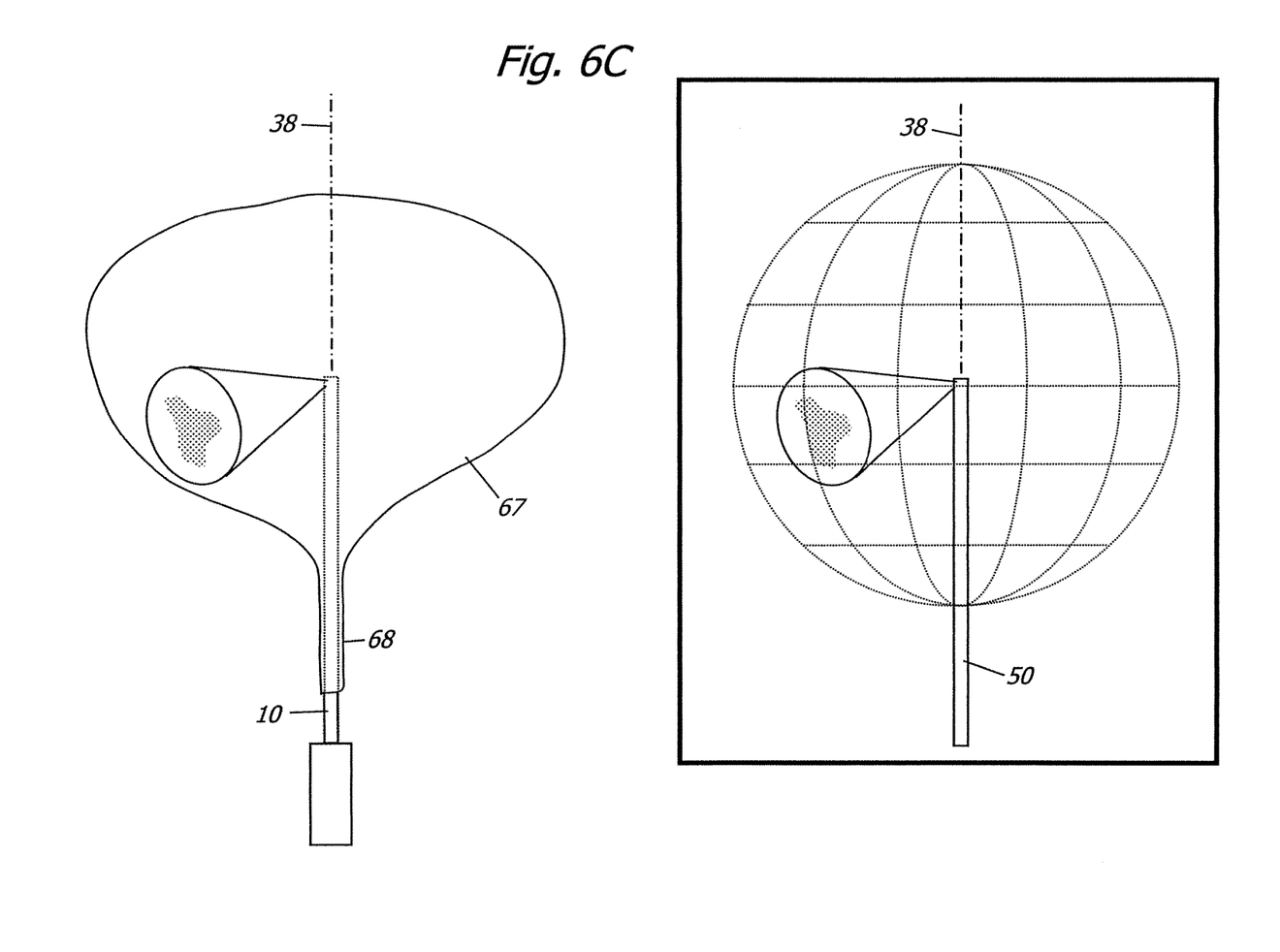
Figure 6D:
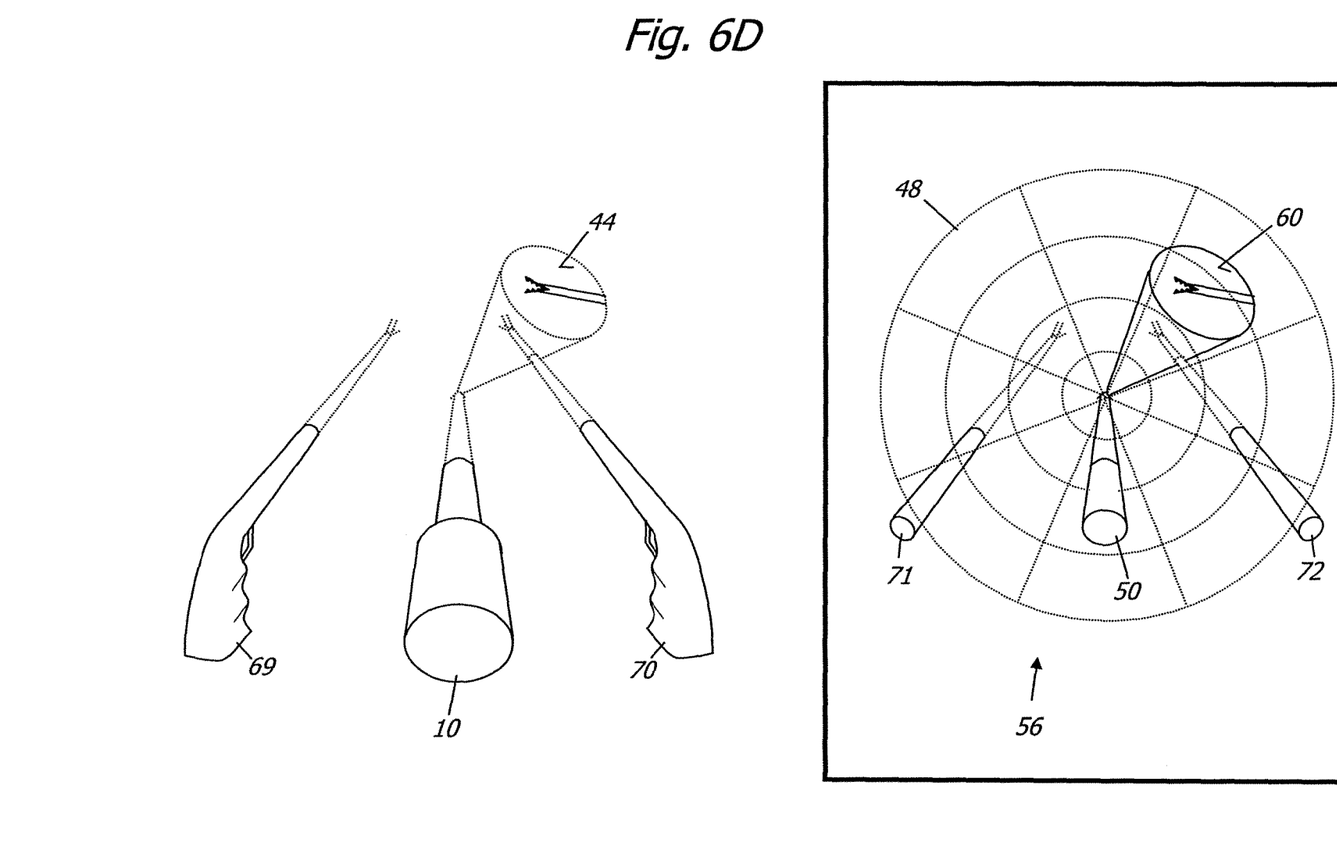
Figure 6E:
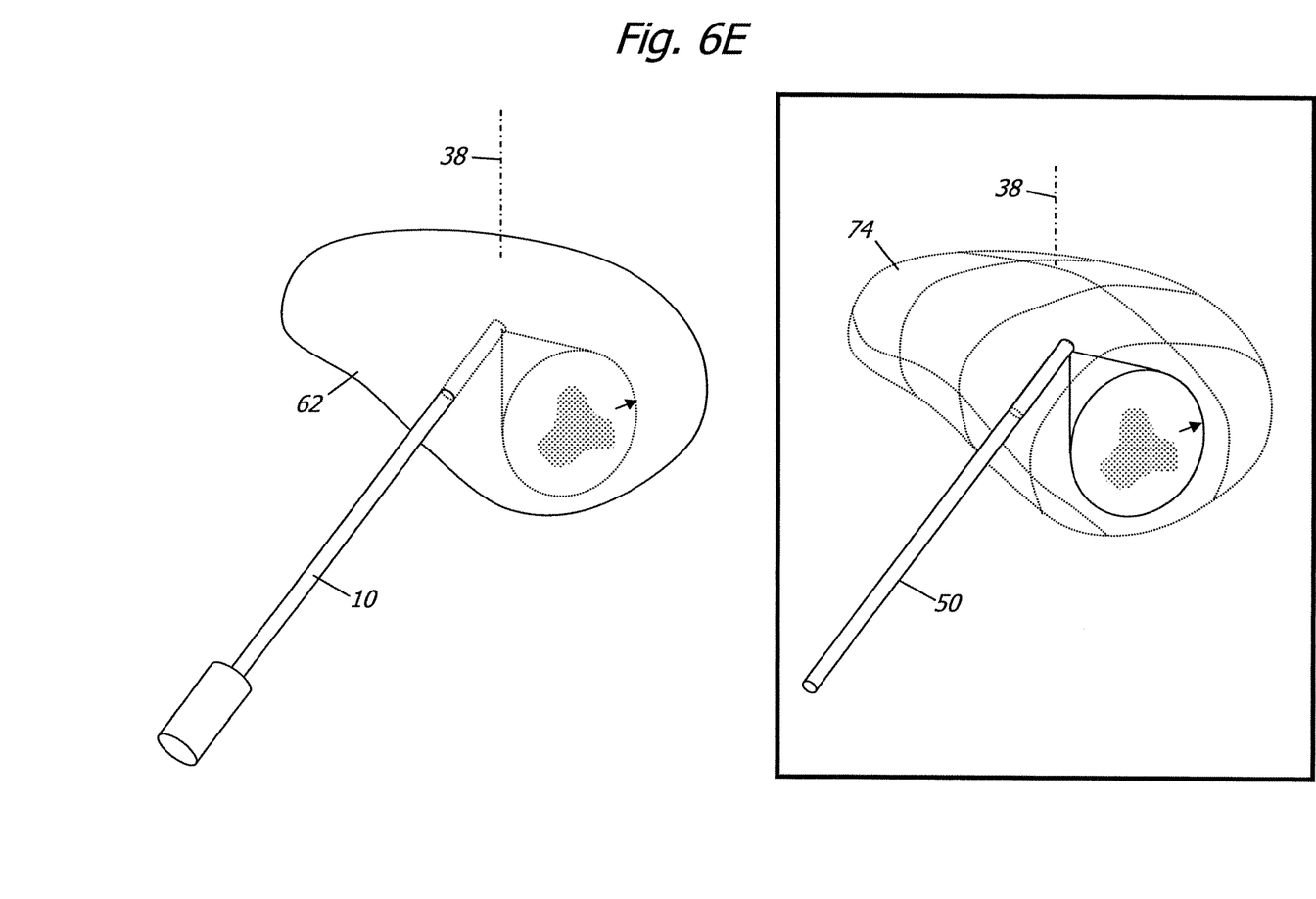

This is particularly useful in surgery, where each procedure typically has a standard configuration. For example, in neuroendoscopy the surgeon typically stands directly behind and above the crown of the patient's head 64, yielding a view as shown in FIG. 6A. The neurosurgeon usually likes to think of local vertical as aligned with an axis normal to the coronal plane, as represented by the alignment of the world 56. In rhinoscopy the patient is typically prone, and the endoscope 10 is inserted at an angle through the patient's nose 66. In this case the surgeon's viewpoint will be behind and slightly to the side of the endoscope 10, suggesting. that the world 56 be oriented as shown in FIG. 6B (Note that there will not necessarily be a correlation between the size of the actual view 16 and the textured image 60). Hysteroscopy or cystoscopy is also often done on prone patients, but in these cases the endoscope 10 is inserted horizontally into the uterus or bladder 67 with the surgeon's viewpoint being above the endoscope 10, giving the orientation illustrated in FIG. 6C. Here the surgeon will usually think of vertical as aligned with the axis of the urethra 68, even though this is a horizontal direction relative to the surgeon. In laparoscopy the surgeon traditionally uses a triangular configuration with the scope 10 in the center and tools 69, 70 on either side, producing the arrangement shown in FIG. 6D. In this case it could be useful for the virtual world 56 to also include virtual tools 71, 72. Unless stereotactic or other sensing means were available, the operator would manually arrange the virtual tools 71, 72 to approximate their actual physical arrangement or use prearranged settings provided by the computer. Also, regardless of the surgical specialty, substituting the navigation coordinate system with a wire frame representation of the anatomy 74, as shown in FIG. 6E, would further aid the operator's understanding of the endoscopic viewing process. Such anatomical representations 74 could come from patient specific preoperative noninvasive scans such as MRI or ultrasound, or from a preexisting library of computer graphical models and would thus provide a realistic size scale.

Figure 7:
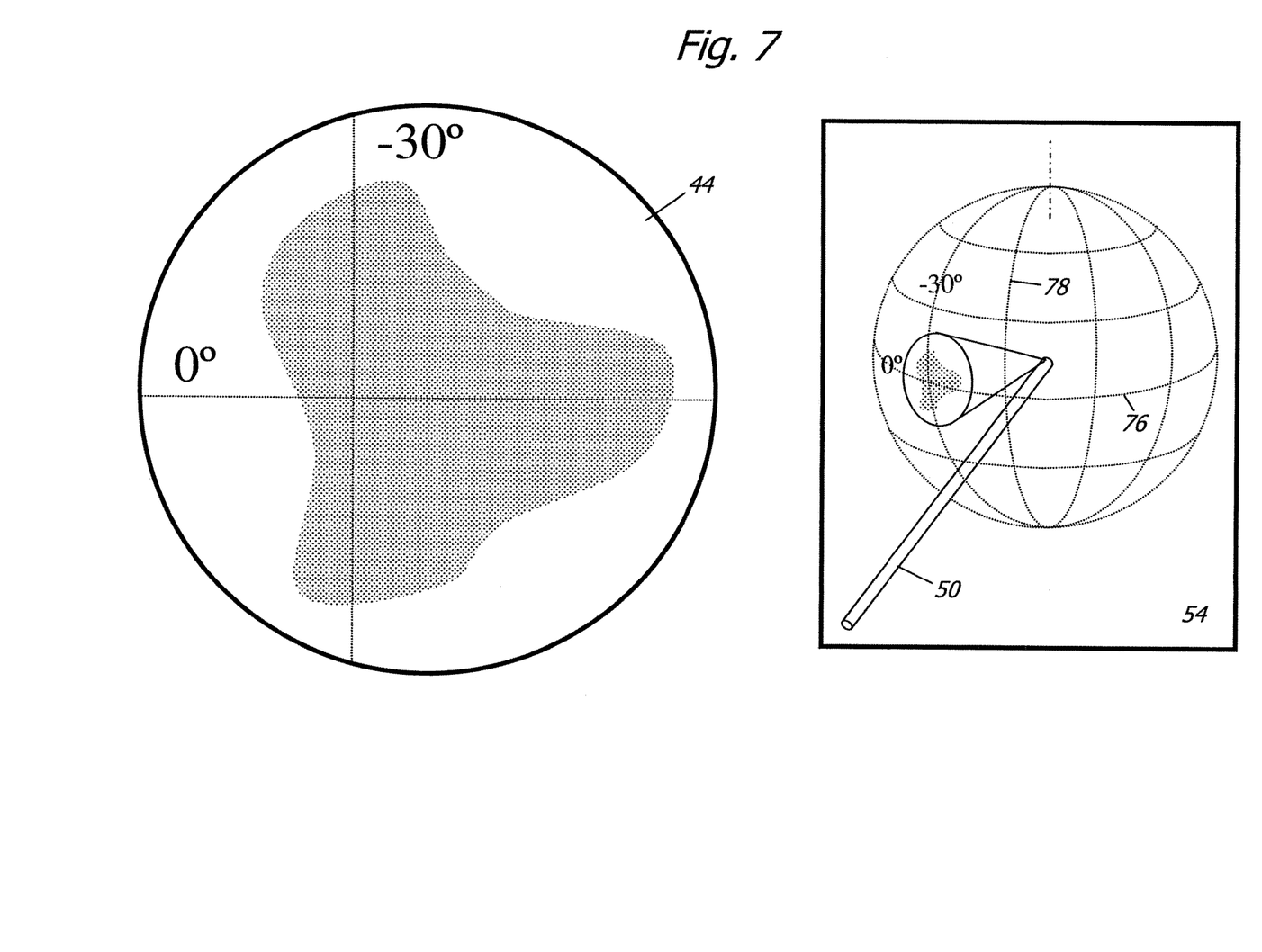
FIG. 7 illustrates the method of displaying global navigation coordinates for indicating the position of the endoscopic view.

Another navigation practice which is very useful for variable direction of view endoscopy is displaying the angular position of the view numerically on or near the endoscopic image 44. This technique is shown in FIG. 7 where the numbers indicate the latitudinal and longitudinal position of the view relative to the equator and a defined zero-meridian, respectively. These numbers could also be displayed in the periphery to not interfere with the endoscopic image 44. If a virtual world 56 were used in support of the image 44, relevant gridlines could be accompanied by their appropriate coordinate numbers and the equator 76 and zero-meridian 78 could be indicated. This practice is similar to naval navigation where positions are indicated by number pairs giving latitudinal and longitudinal position relative to the equator and the Greenwich meridian.

Accordingly, the present invention provides a dynamic representation of the endoscopic viewing direction featuring a live image icon and an adjustable virtual world. It also provides real time numerical indications of the global position of the view relative to the virtual equator and zero-meridian.

The present invention has been described above in terms of a presently preferred embodiment so that an understanding of the invention may be conveyed. However, many alternative presentations, designs, and implementations are possible without departing from the principle of the invention. For example, the present invention would also be useful with fixed-angle scopes with sensors for detecting the attitude of the endoscope shaft. Further, this invention works equally well with flexible endoscopes instrumented in such a way that their shaft configurations are known. The scope of the present invention should therefore not be limited by the embodiments illustrated, but rather it should be understood that the present invention has wide applicability with respect to variable direction viewing instruments. All modifications, variations, or equivalent elements and implementations that are within the scope of the appended claims should therefore be considered within the scope of the invention.

We claim:

1. A method for representing an endoscopic view and viewing direction, the method comprising:
    acquiring images with an endoscope having a distal end and a view vector that pivots relative to the distal end, the view vector having an attendant view cone that defines a current image;
    displaying the current image in a first section of a display;
    sensing the attitude of the endoscope using sensors attached to the endoscope;
    displaying, in a second section of the display different from the first section of the display and simultaneously with the current image, a virtual representation of an endoscopic environment comprising a graphical representation of the endoscope, a texture mapped version of the current image defined by the view cone, and a graphical representation of a navigation coordinate system in which said graphical representation of the endoscope and texture mapped image are arranged in positions based on the attitude of the endoscope;
    updating the texture mapped image as the view cone moves through a solid angle as the view vector pivots; and
    updating the positions of the updated texture mapped image and the graphical representation of the endoscope within the graphical representation of the navigation coordinate system as the view cone moves through a solid angle as the view vector pivots.

2. The method of claim 1, wherein the graphical navigation coordinate system defines a globe.

3. The method of claim 1, wherein the virtual representation of the endoscopic environment comprises a wire framed representation of an anatomical structure.

4. The method of claim 1, further comprising displaying a number that indicates the viewing direction on the display on the current image.

5. The method of claim 1, further comprising displaying a graphical representation of the direction of gravity on the display of the current image.

6. The method of claim 1, wherein the virtual representation includes a graphical representation of the direction of gravity.

7. The method of claim 1, wherein said virtual representation includes a graphical representation of at least one tool relative to the endoscope, the view cone, and the texture mapped version of the image.

8. The method of claim 1, wherein the virtual representation of the endoscopic environment is at least partly based on volumetric data obtained from a non-invasive imaging technique.

9. The method of claim 8, wherein the volumetric data is obtained from magnetic resonance imaging.

10. The method of claim 8 wherein the volumetric data is obtained from ultrasound.

11. The method of claim 1, further comprising:
    projecting at least a portion of the navigation coordinate system on the display of the current image that corresponds to the graphical representation of the navigation coordinate system of the virtual representation of the endoscopic environment.

12. The method of claim 1, further comprising:
    displaying, within the virtual representation of the endoscopic environment, a graphical representation of the view cone arranged in a position within the graphical representation of the navigation coordinate system based on the attitude of the endoscope; and
    updating the position of the graphical representation of the view cone within the graphical representation of the navigation coordinate system as the view cone moves through a solid angle as the view vector pivots.

* * * * *